United States Patent [19]

Wiegers et al.

[11] Patent Number: 4,524,021
[45] Date of Patent: Jun. 18, 1985

[54] PERFUMERY USES OF ESTERS OF PHENYL ALKANOLS

[75] Inventors: Wilhelmus J. Wiegers, Red Bank; Mark A. Sprecker, Sea Bright, both of N.J.

[73] Assignee: International Flavors & Fragrances Inc., New York, N.Y.

[21] Appl. No.: 617,585

[22] Filed: Jun. 5, 1984

Related U.S. Application Data

[62] Division of Ser. No. 491,657, May 5, 1983.

[51] Int. Cl.$^3$ .................... A61K 7/46; C11B 9/00
[52] U.S. Cl. ............................................ 252/522 R
[58] Field of Search ................................. 252/522 R

[56] References Cited

U.S. PATENT DOCUMENTS 4,113,781  9/1978  Aquila et al. ............... 252/522 R

FOREIGN PATENT DOCUMENTS 56500  7/1982  European Pat. Off. ............ 254/

OTHER PUBLICATIONS

Chemical Abstracts 91 198681t, (1979).
Arctander, Perfume & Flavor Chemicals, N.J., vol. I Monograph 1705, vol. II Monographs 2512, 2189, 2588 and 2539, (1969).

*Primary Examiner*—Helen M. S. Sneed
*Attorney, Agent, or Firm*—Arthur L. Liberman

[57] ABSTRACT

Described is a method for producing the compounds described according to the structure:

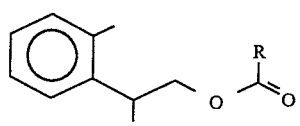

wherein R represents ethyl or methyl as well as optical isomers thereof having the structures:

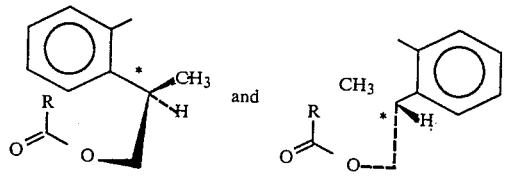

wherein R represents methyl or ethyl, as well as uses thereof in augmenting or enhancing the aroma of perfume compositions, colognes and perfumed articles such as perfumed polymers and solid or liquid anionic, cationic, nonionic or zwitterionic detergents, fabric softener compositions and fabric softener articles. Also described are processes and compositions for use in perfume aroma augmenting, enhancing, modifying and altering compositions and as perfume, cologne and perfumed article aroma imparting compositions of mixtures of the compounds defined according to the structure:

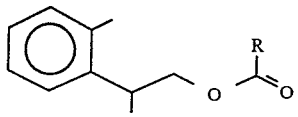

wherein R represents methyl or ethyl taken further together with the alcohol having the structure:

(Abstract continued on next page.)

with one or more butanoyl cyclohexane derivatives and/or 3-methyl-1-phenyl-pentanol-5. The process for preparing the compounds having the structure:

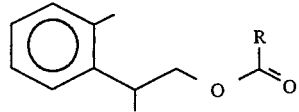

wherein R represents methyl or ethyl involves a two-step reaction wherein the compound having the structure

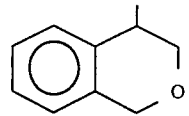

is hydrogenated in the presence of acid to form the alcohol having the structure

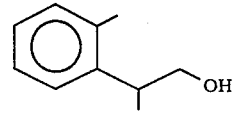

and the resulting alcohol is then esterified.

2 Claims, 7 Drawing Figures

GLC PROFILE FOR EXAMPLE I.

NMR SPECTRUM FOR FRACTION 10 OF EXAMPLE I.

IR SPECTRUM FOR FRACTION 10 OF EXAMPLE I.

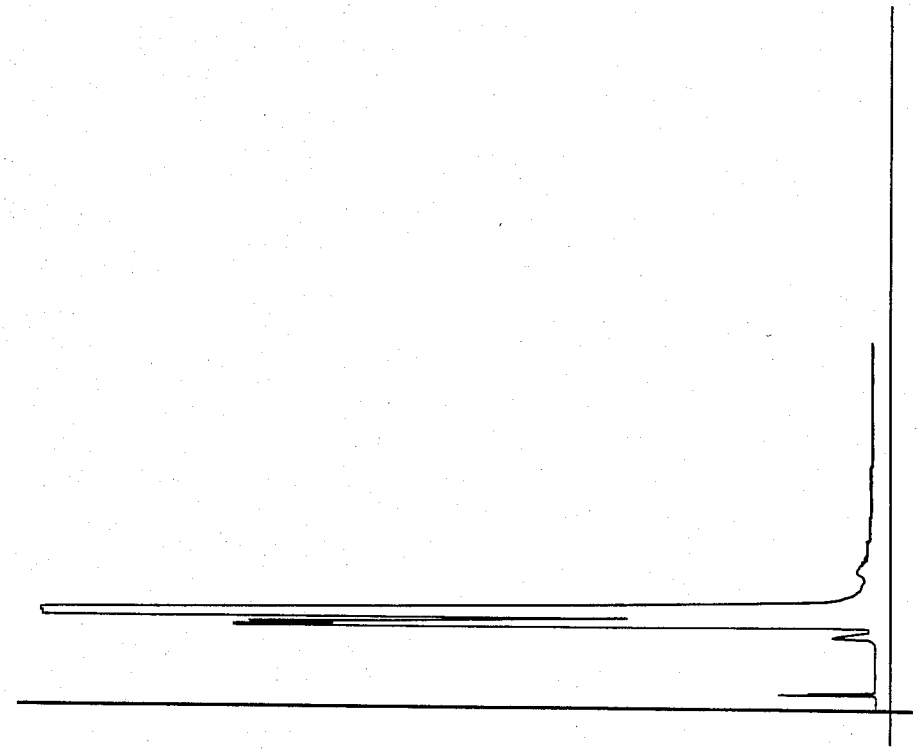
FIG.5 GLC PROFILE FOR FRACTION 9 OF EXAMPLE II.
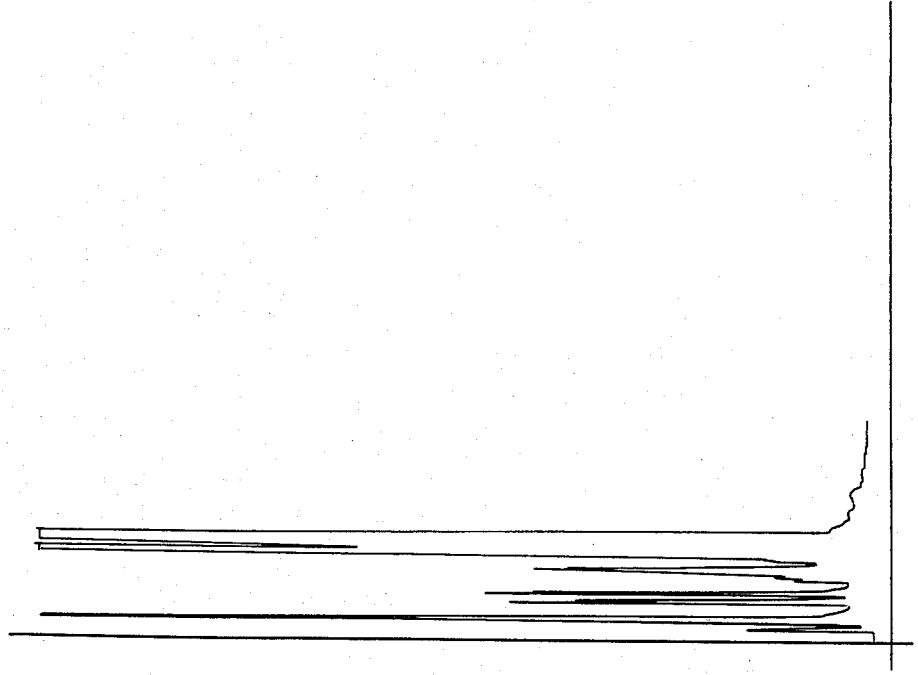
FIG.4 GLC PROFILE FOR EXAMPLE II CRUDE

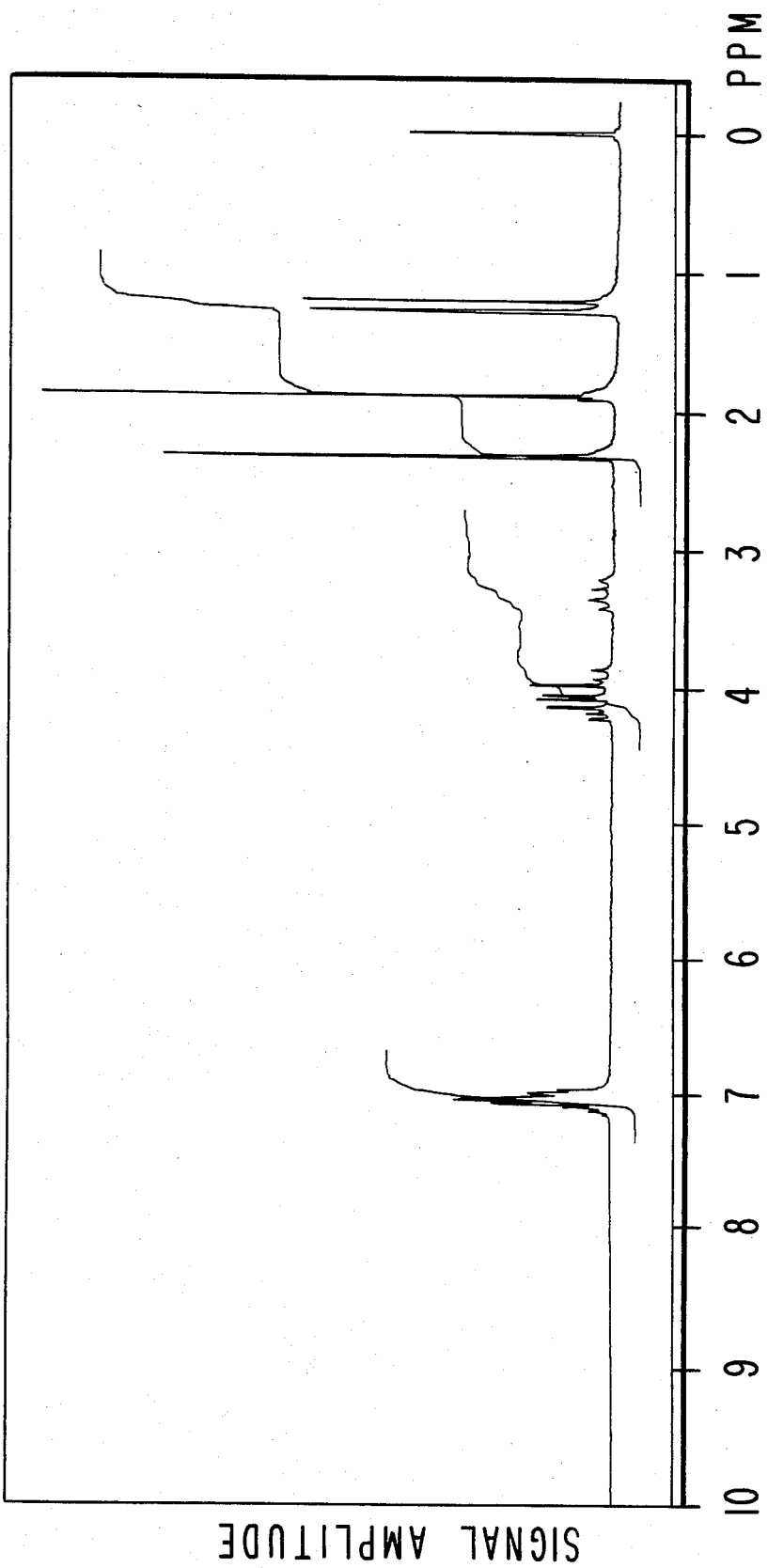
FIG. 6 NMR SPECTRUM FOR FRACTION 9 OF EXAMPLE I.

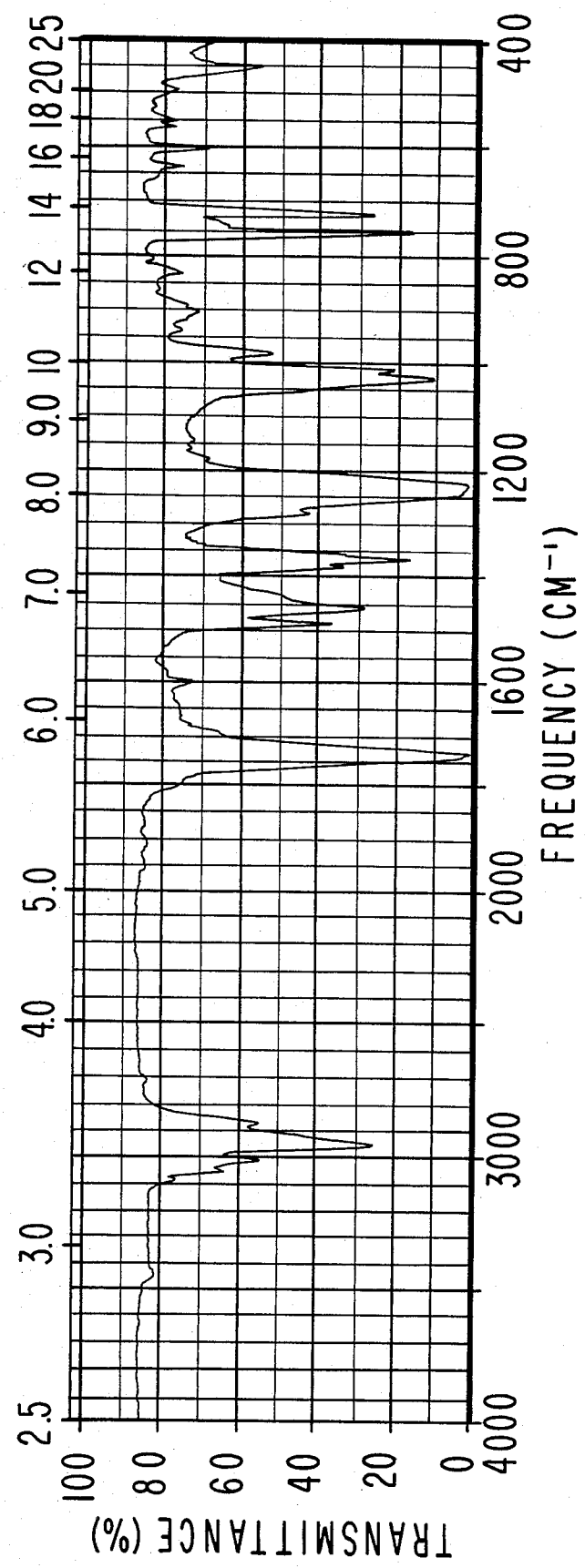

PERFUMERY USES OF ESTERS OF PHENYL ALKANOLS

This is a divisional of application Ser. No. 491,657, filed 5.5.83.

BACKGROUND OF THE INVENTION

The present invention relates to the use in augmenting, enhancing or modifying the aroma of perfume compositions, colognes and perfumed articles of the compounds defined according to the structure:

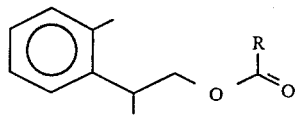

wherein R represents methyl or ethyl taken alone or taken further together with the alcohol having the structure:

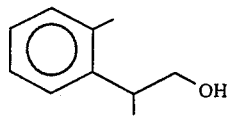

and/or butanoyl cyclohexane derivatives defined according to the structure:

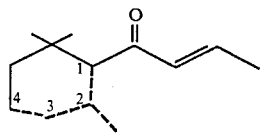

wherein one of the dashed lines is a carbon-carbon double bond or two of the dashed lines are carbon-carbon double bonds (but that when two of the dashed lines represent carbon-carbon double bonds, the carbon-carbon double bonds are conjugated) and/or 3-methyl-1-phenyl-pentanol-5 having the structure:

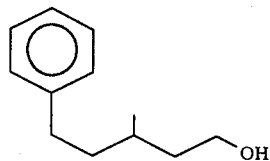

The present invention also relates to a process for preparing the compounds defined according to the structure:

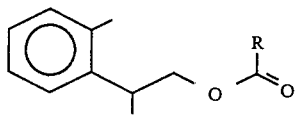

wherein R represents methyl or ethyl, by means of first reacting the compound having the structure:

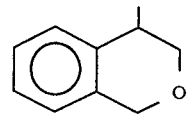

with hydrogen in the presence of acid to form an alcohol having the structure:

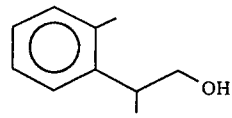

and then esterifying the resulting alcohol to form esters defined according to the structure:

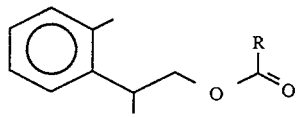

There has been considerable work performed relating to substances which can be used to impart (or alter, modify or enhance) fragrances to (or in) perfume compositions, colognes or perfumed articles such as solid or liquid anionic, cationic, nonionic or zwitterionic detergents, fabric softener compositions and fabric softener articles as well as perfumed polymers. These substances are used to diminish the use of natural materials some of which may be in short supply and/or to provide more uniform properties to the finished product.

Strong, long-lasting, green, floral, peony-like, rosey, hyacinth-like and lilac aroma nuances with anise-like undertones are desirable in many types of perfume compositions, perfumes and perfumed articles.

Phenylethyl acetate, p-methyl-phenethyl acetate, phenyl propyl acetate, phenylethyl methyl carbinyl acetate and hydratropic acetate are well known aryl alkanol esters having known uses in augmenting or enhancing rose aromas in perfume compositions, colognes and perfumed articles. Reference is made to the monographs concerning these compounds in the text Arctander, "Perfume and Flavor Chemicals (Aroma Chemicals)", Volumes I and II, to wit:

2512: PHENYLETHYL ACETATE beta-Phenethylacetate

2-Phenylethyl acetate

Benzyl carbinyl acetate

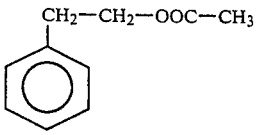

$C_{10}H_{12}O_2 = 164.21$

Colorless oily liquid. Sp.Gr. 1.05. B.P. 232° C.
Very slightly soluble in water, soluble in alcohol, Propylene glycol and oils.

Very sweet, rosy-fruity, honey-like odor of moderate to poor tenacity. The fruity notes are mostly peachy with a pleasant leafy-green tonality, the rosy notes very sweet, almost towards Gardenia. Variations in the odor of this material will naturally follow the pattern of the parent alcohol in which sharper, more pungent notes are typical of the commercial grades, while warm, deep-rosy notes will balsamic softness are typical of the highly refined grades.

The taste at concentrations below 10 ppm is sweet, fruity-honey-like, remotely Raspberry-like, but at higher levels rather "perfumey" not quite attractive.

The title ester is widely used in perfume compositions, from everyday soap and detergent perfumes to fine cosmetic fragrances, room-sprays, deodorants, etc. almost any type of perfume. Its sweetness, versatility and very low cost makes it almost universally applicable. For Rose, Jasmin, Hyacinth, Reseda, Freesia, Peony, Magnolia, Oriental and even citrusy fragrance types, it may be used at concentrations from 1 percent up to 10 or perhaps much higher.

The title ester is also commonly used in flavor compositions, for imitation Butter, Apple, Apricot, Caramel, Honey, Passion-fruit, Peach, Strawberry and fruit complexes, Vanilla flavors, floral and Rose type flavors, etc.

The concentration in the finished product is normally as low as 1 to 6 ppm.

G.R.A.S. F.E.M.A. No.2857.

Prod.: by direct esterification of Phenylethylalcohol with Acetic acid or Acetic anhydride.

31–125; 33–502; 26–654; 61–71; 106–292; 140–136; 90–333; 156–311; 163–62; 163–232; B-VI-479;

2189: para-METHYL PHENYLETHYL ACETATE 2-para Tolyl ethyl acetate beta-para-Tolyl ethyl acetate "Fliedenol acetate"

"Syringa alcohol, Acetate"

(An isomer of Methyl phenyl carbinyl propionate).

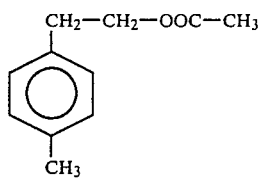

$C_{11}H_{14}O_2 = 178.23$

Colorless oily liquid. Sp.Gr. 1.03. B.P. 233° C.

Almost insoluble in water, soluble in alcohol and oils.

Sweet and relatively pleasant, floral odor of moderate tenacity. The floral notes resemble Lilac and Mimosa.

This ester, usually marketed under trade names, finds use in perfume compositions, mainly soap perfumes of the floral or floral-Oriental type. It is inexpensive and stable, non-discoloring, and sufficiently mild that large proportions can be used without the appearance of dominating or unpleasant notes. It seems to improve the Lilac effect of Terpineol and it can link it pleasantly to Dimethyl benzyl carbinol or related materials. It is not confined to Lilac compositions, and Hydroxycitronellal or Cyclamenaldehyde, or even the "rose alcohols" may blend with this ester into quite a wide range of other floral fragrance types.

Prod.: from para-Tolyl Magnesium bromide plus Ethylene chlorhydrin followed by Acetylation of the alcohol.

86–129;

2588: 3-PHENYL PROPYL ACETATE

Hydrocinnamyl acetate.

beta-Phenylpropyl acetate (this name is confusing but frequently used in perfumery literature).

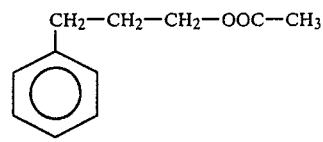

$C_{11}H_{14}O_2 = 178.23$

Colorless liquid. Sp.Gr. 1.02.

Very slightly soluble in water, soluble in alcohol and oils.

Sweet, floral-fruity, warm and mildly balsamic odor of moderate tenacity.

Pleasant, balsamic-fruity sweet taste in concentrations below 20 ppm.

This ester is used in perfume compositions as a modifier in Hyacinth, Rose, Oriental bases, Lilac and Lily, Reseda, etc. and it blends well with the "rose alcohols", the Linalool family, Styrax and Ylang, Labdanum, Amylsalicylate, etc. Its neutral sweetness makes it very versatile, but it does not lend much odor power to a composition.

Smaller amounts are used in spice flavors, fruit complexes and certain types of berry flavor, including Cherry. The concentration used in such flavors is equivalent to 0.5 to 10 ppm in the functional product.

G.R.A.S. F.E.M.A. No.2890.

Prod.: by azeotropic esterification of Phenylpropyl alcohol with Acetic acid.

28–659; 33–503; 34–581; 69–71; 106–305; 140–137;

2539: PHENYLETHYL METHYL CARBINYL ACETATE

4-Phenyl-2-butanol acetate (Not to be confused with Butyl phenylacetate)

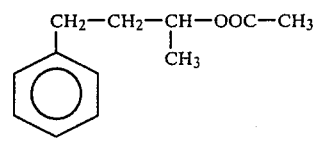

$C_{12}H_{16}O_2 = 192.26$

Colorless liquid.

Practically insoluble in water, soluble in alcohol and oils.

Mild and fresh, slightly green, fruity and sweet odor of moderate tenacity.

Sweet fresh-fruity, mild taste with a green, peel-like note in concentrations below 10 ppm.

The title ester is, to the author's knowledge, not used commonly in perfumes.

It finds some use in flavor compositions of the Peach, Apricot and Mango type, where it blends excellently with Undecalactone and alkyl caproates, etc.

The normal concentration in finished products will be as low as 0.2 to 5 ppm.

G.R.A.S. F.E.M.A. No.2882

Prod.: by azeotropic esterification of Phenylethyl methyl carbinol with Acetic acid. 61-71;

1705: HYDRATROPYL ACETATE alpha-Phenylpropyl acetate alpha-Methyl phenyl acetate 2-Phenyl propylacetate

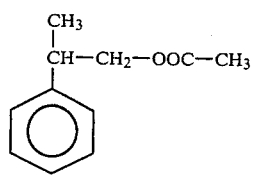

$C_{11}H_{14}O_2 = 178.23$

Colorless liquid. Sp.Gr. 1.07.

Almost insoluble in water, soluble in alcohol, miscible with oils. Fairly soluble in Propylene glycol.

Fresh-floral powerful and fruity-green, slightly earthy-green odor more delicate than Phenylethylacetate, not as rosy, more Hyacinth-Lilac-like. Inspite of its power, or rather "lift", its effect is almost a delicate one, enabling the perfumer to use 2-4.6% of this ester in floral bases where green or green-earthy or spicy notes are already composed or called for.

The ester finds use in Hyacinth, Lilac, Ylang-Ylang, Narcisse, etc. as well as in Oriental blends, where it gives pleasant combinations with the Phenylacetates or Cinnamates, particularly soothing on Methyl-cinnamate.

Prod.: by direct esterification of Hydratropyl alcohol with Acetic acid under azeotropic conditions, or with Acetic anhydride.

4-63; 34-583; 86-61; (sample: I.F.F.).

The compound defined according to the structure:

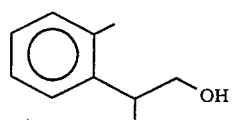

is known but its ester as well as its ester's use in perfumery has heretofore been unknown. The synthesis of the compound having the structure:

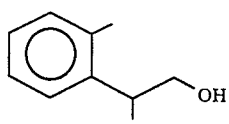

was heretofore known by means of a complex and cumbersome reduction of the corresponding carboxylic acid according to the reaction:

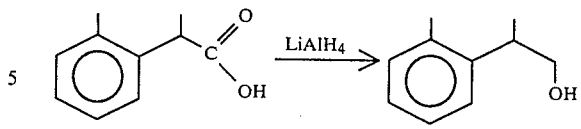

(Kusowkow, Zh. Obshch. Chim. 28 [1958] 2283,6).

U.S. Pat. No. 4,210,554 discloses fragrance compositions containing 3-methyl-1-phenyl-pentanol-5 or specific optical isomers thereof and one or more butanoyl cyclohexane derivatives. It is indicated in U.S. Pat. No. 4,210,554 that woody, rosy, green and earthy notes are desirable and augmented or enhanced in many types of perfume compositions, perfumes and perfumed articles by 3-methy-1-phenyl-pentanol-5 and one or more butanoyl cyclohexane derivatives defined according to the structure:

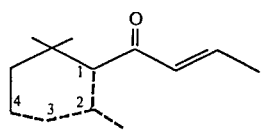

wherein one of the dashed lines is a carbon-carbon double bond or two of the dashed lines are carbon-carbon double bonds but when two of the dashed lines represent carbon-carbon double bonds, the carbon-carbon double bonds are conjugated.

U.S. Pat. No. 4,028,279 entitled "Novel Fragrance Composition Containing 2,6,6-Trimethyl-1-Cyclohexene-1-yl Acetaldehyde and Phenyl $C_6$ Ketone" relates to mixtures of (i) either or both of the phenyl $C_6$ ketones, 2,5-phenylhexen-1-one-3 and (ii) 2,2,6-trimethyl-1-cyclohexen-1-yl acetaldehyde used to alter, modify, enhance or impart aromas in or to perfumes, perfume compositions and/or perfumed articles. It is disclosed in said U.S. Pat. No. 4,028,279 that such perfume compositions containing such mixtures have intense rosy aromas with woody, green and earthy notes. The structure of the phenyl $C_6$ ketones disclosed in U.S. Pat. No. 4,028,279 is:

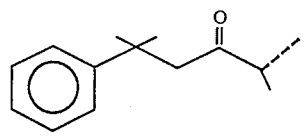

the structure of the betacyclohomocitral used in U.S. Pat. No. 4,028,279 is:

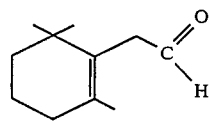

wherein the dashed line may be either a carbon-carbon single bond or a carbon-carbon double bond.

In U.S. Pat. No. 3,595,508, issued on May 25, 1976, mixtures of (i) 2,2,6-trimethyl-1-cyclohexen-1-yl acetaldehyde and (ii) 2,6,6-trimethyl crotonyl-1,3-cyclohexadiene having the structure:

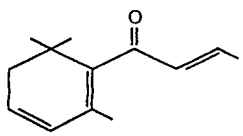

are indicated to produce in perfumes rosy, woody, camphoraceous, green and earthy notes.

Nothing in the prior art including U.S. Pat. Nos. 4,210,554, 3,959,508 and 4,028,279 imply or state that such mixtures are as disclosed and claimed in the instant case can be used to enhance and extend specific green, floral, peony-like, rosey, hyacinth and lilac nuances with anise-like undertones. Nothing in the prior art discloses a process for producing the compounds defined according to the structures:

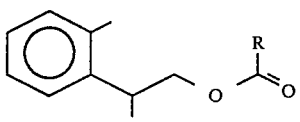

wherein R represents methyl or ethyl, prepared using the reaction:

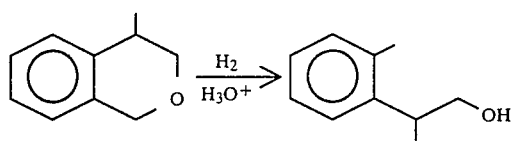

and the reaction:

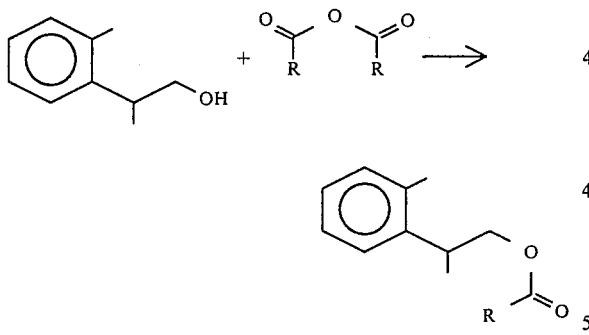

wherein R represents methyl or ethyl. Nothing in the prior art discloses the unexpected, unobvious and advantageous perfumery properties of the compounds defined according to the structure:

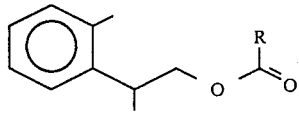

wherein R represents methyl or ethyl.

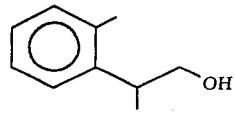

(conditions: 10% Carbowax column, 0.25"×10'; programmed at 80°-225° C. at 8° C. per minute).

Figure 2:
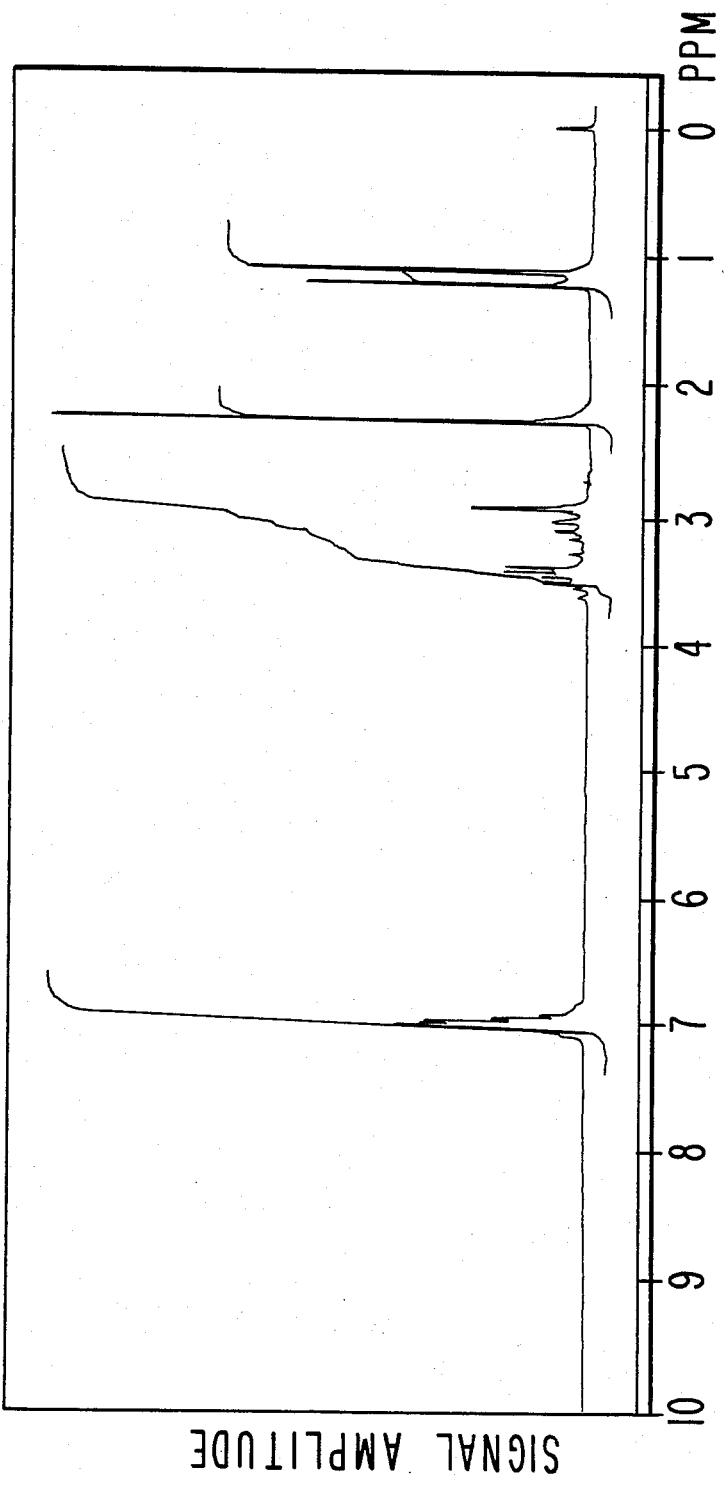

FIG. 2 is the NMR spectrum for fraction 10 of the distillation product of the reaction product of Example I containing the compound having the structure:

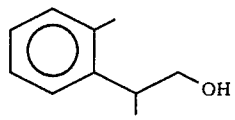

Figure 3:
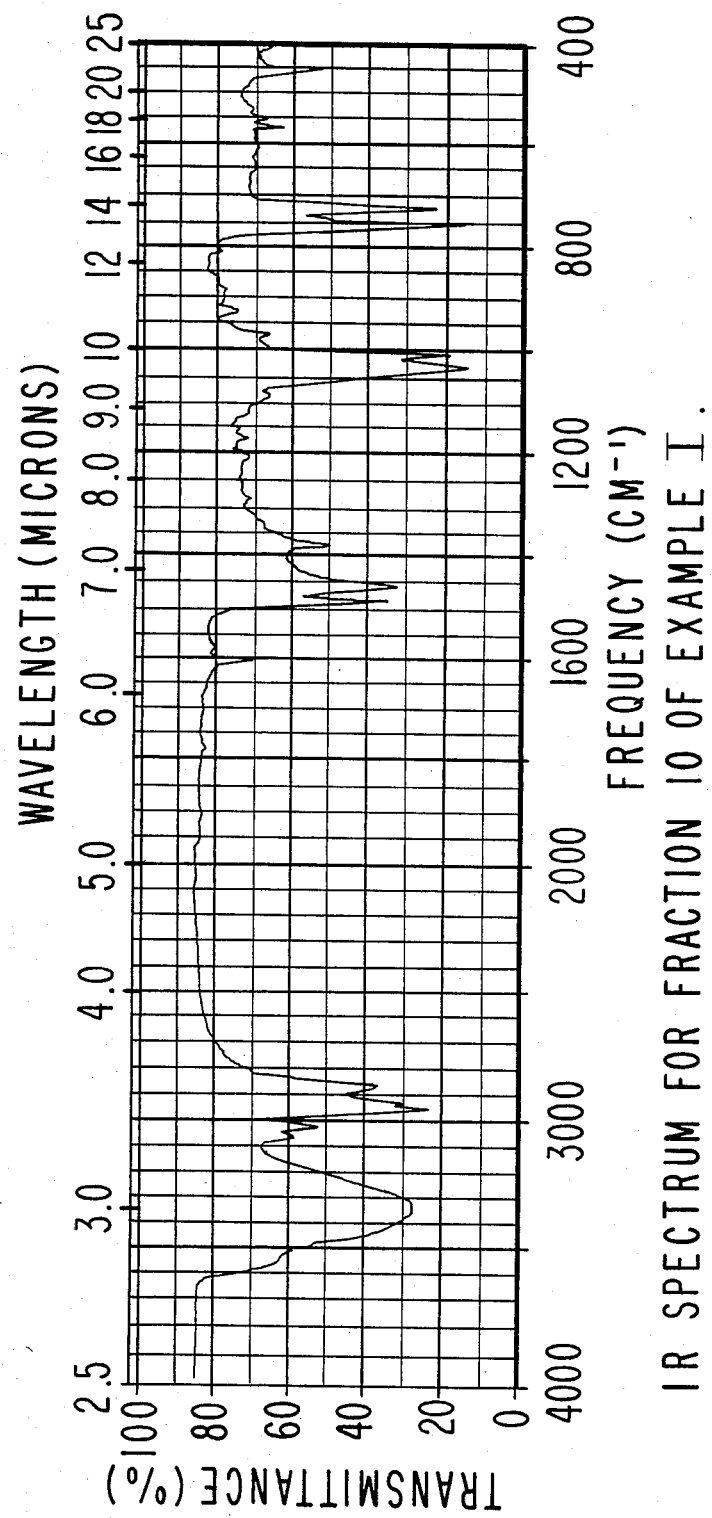

FIG. 3 is the infra-red spectrum for fraction 10 of the distillation product of the reaction product of Example I containing the compound having the structure:

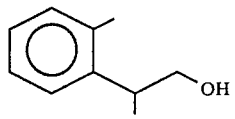

FIG. 4 is the GLC profile of the crude reaction product produced according to Example II containing the compound defined according to the structure:

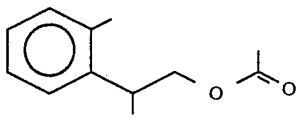

FIG. 5 is the GLC profile for fraction 9 of the distillation product of the reaction product of Example II containing the compound having the structure:

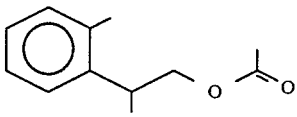

(conditions: SE-30 column programmed at 200° C., isothermal).

FIG. 6 is the NMR spectrum for fraction 9 of the distillation product of the reaction product of Example II containing the compound having the structure:

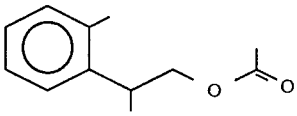

(conditions: CFCl$_3$ solvent; 100 MHz field strength).

FIG. 7 is the infra-red spectrum for fration 9 of the distillation product of the reaction product of Example II containing the compound having the structure:

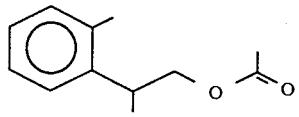

THE INVENTION

It has now been discovered that novel perfume compositions and perfumed articles as well as colognes having extended long-lasting, highly intense and natural-like green, rose, peony-like, floral, hyacinth and lilac nuances with anise-like undertones may be provided by the utilization of one or both of the compounds defined according to the structure:

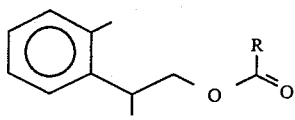

wherein R represents methyl or ethyl, as well as by utilization of mixtures of one or both of the compounds defined according to the structure:

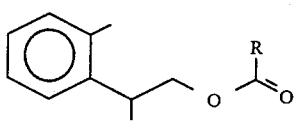

wherein R represents methyl or ethyl, and (i) the compound having the structure:

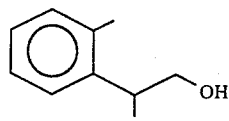

and/or (ii) one or more butanoyl cyclohexane derivatives having the structure:

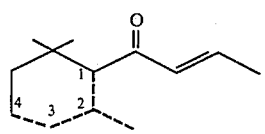

where one or two of the dashed lines is a carbon-carbon double bond and the other of the dashed lines are carbon-carbon single bonds with the proviso that if two of the dashed lines are carbon-carbon double bonds, the carbon-carbon double bonds are conjugated and/or (iii) 3-methyl-1-phenyl-pentanol-5 racemic mixtures or individual stereoisomers having one of the structures:

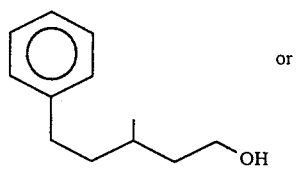

or

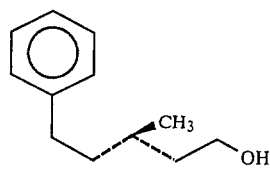

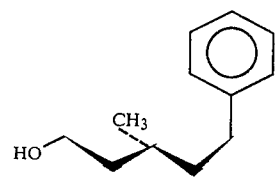

It has also been discovered that the compounds defined according to the structure:

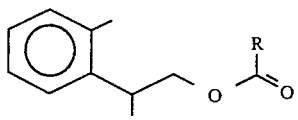

wherein R represents methyl or ethyl, may be prepared by a highly cost effective process, specifically by means of (i) first reacting the compound defined according to the structure:

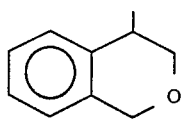

with hydrogen in the presence of acid according to the reaction:

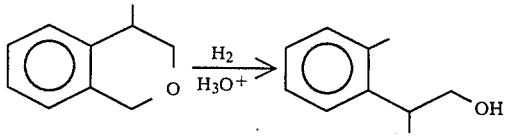

and then esterifying the resulting alcohol by means of standard esterification techniques according to the reaction:

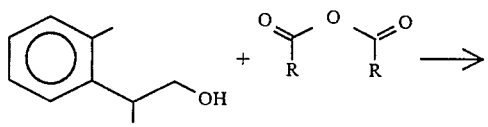

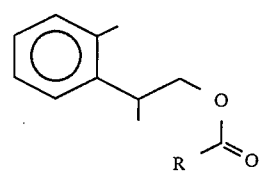

wherein R represents methyl or ethyl.

Included in the compounds defined according to the structure:

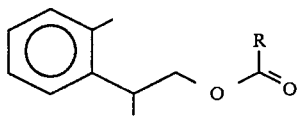

wherein R represents methyl or ethyl, are the optical isomers thereof defined according to the structures:

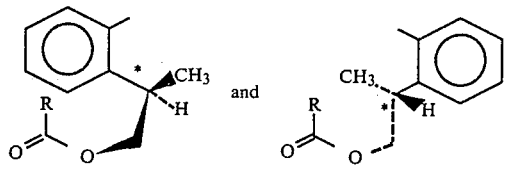

In carrying out the foregoing hydrogenation reaction (i) various hydrogenation catalysts may be used, for example, palladium, platinum and palladium-on-carbon, for example 3% up to 20% palladium-on carbon. The reaction is carried out in the presence of a catalytic quantity of mineral acid, for example, phosphoric acid, sulfuric acid, hydrochloric acid and paratoluenesulfonic acid. The reaction temperature may be in the range of from about 25° C. up to about 150° C. The reaction pressure is in the range of from about 50 psig up to about 1000 psig. The weight ratio of hydrogenation catalyst, e.g. palladium-on-carbon:mineral acid, e.g. phosphoric acid, may vary from about 0.1:1 up to about 1:0.1 with a preferred weight ratio of about 1:1.

The hydrogenation reaction preferably takes place in the presence of a solvent which is inert to the reactants, for example, isopropyl alcohol, n-propyl alcohol, ethanol, benzene and toluene. At the end of the reaction, the reaction mass is filtered, stripped of solvent and distilled as by fractional distillation. If desired, the reaction product defined according to the structure:

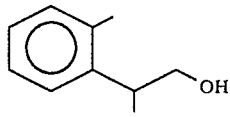

may be used as is for its organoleptic properties or it may be further purified by means of standard "d" and "l" separation, for example, by producing esters from optically active acids such as d or l mandelic acid, separating the resulting stereoisomers by means of fractional crystalization and then hydrolyzing the resulting esters back to the alcohols defined according to the structures:

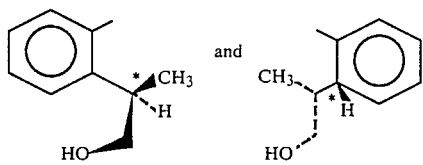

The resulting products are then esterified using standard acylation reagents and conditions, e.g. using acyl halides such as acetyl chloride, acetyl bromide, propionyl bromide and propionyl chloride at temperatures in the range of from about 0° C. up to about 35° C. and acyl anhydrides such as acetic anhydride and propionic anhydride at temperatures in the range of from about 80° C. up to about 180° C.

In perfumes, perfumed articles such as soaps and detergents (solid or liquid anionic, cationic nonionic or zwitterionic detergents), optical brightener compositions, fabric softeners (for example, fabric softener compositions for clothes driers), perfume compositions, colognes and perfumed polymers, it has been discovered by us that green, rose, peony-like, floral, hyacinth and lilac fragrances with anise-like undertones may be augmented or enhanced.

It has further been discovered by us that the organoleptic effect obtained when using mixtures containing at least one of the compounds defined according to the structure:

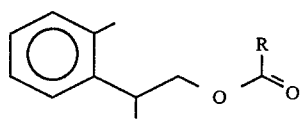

wherein R is methyl or ethyl, taken further together with the compounds having the structure:

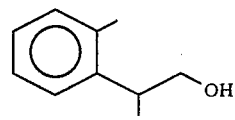

and/or 3-methyl-1-phenyl-pentanol-5 and/or one or more butanoyl cyclohexane derivatives is more than merely additive of the individual organoleptic properties of at least one of the compounds having the structure:

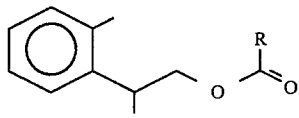

wherein R is methyl or ethyl, taken alone or taken further together with (i) the compound having the structure:

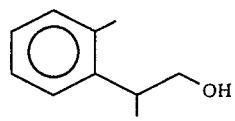

and/or (ii) 3-methyl-1-phenyl-pentanol-5 and/or (ii) butanoyl cyclohexane derivative having the structure:

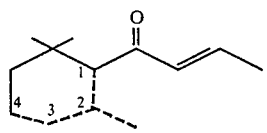

taken alone; and that the additive effect of one of the compounds having the structure:

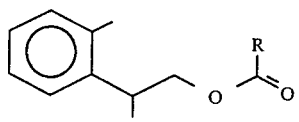

wherein R is methyl or ethyl taken together with 3-methyl-1-phenyl-pentanol-5 and/or one or more butanoyl cyclohexane derivatives having the structure:

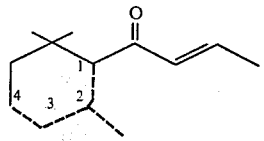

and/or the compound having the structure:

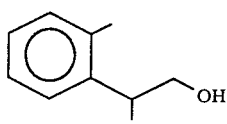

may be described as "synergistic".

The 3-methyl-1-phenyl-pentanol-5-having one of the structures:

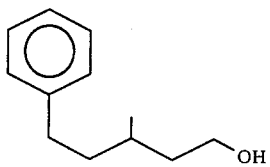

or

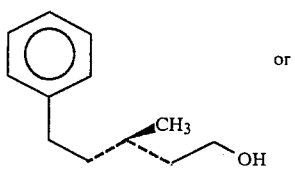

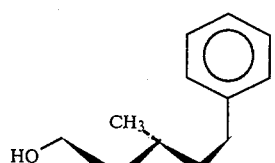

may be prepared according to the procedure described by Rupe Hirschmann and Werdenberg at Helv. Chimica Acta. 18 [1935] at pages 535–42 (abstracted at Beilstein E III 6 1997, H 6, 551).

Methods for preparing the butanoyl cyclohexane derivatives which may be used in our invention are described in Swiss Pat. No. 520,479 issued on May 12, 1972 as well as in application for United States Letters Patent Ser. No. 851,727 filed on Nov. 15, 1977, now United States Letters Pat. No. 4,211,242.

Contemplated within the scope of our invention are mole ratios of compound having the structure:

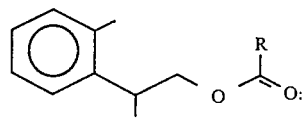

compound having the structure:

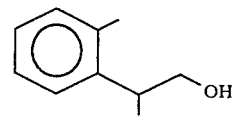

and/or butanoyl cyclohexane derivative having the generic structure:

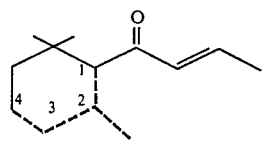

and/or 3-methyl-1-phenyl-pentanol-5 of from about 0.01:1 up to about 1:1 (mole ratio). It is however preferable in the practice of our invention to use mole ratios of compound having the structure:

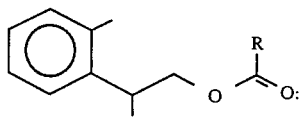

compound having the structure:

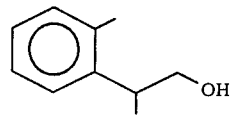

and/or butanoyl cyclohexane derivative and/or 3-methyl-1-phenyl-pentanol-5 derivative of from about 0.1:1 up to about 0.2:1.

When at least one of the compounds defined according to the structure:

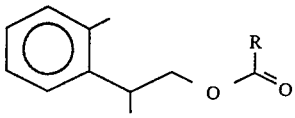

wherein R is methyl or ethyl, or mixtures of compounds having the structure:

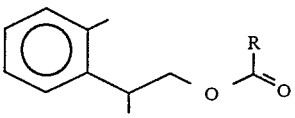

and (i) compound having the structure:

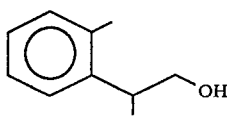

and/or (ii) 3-methyl-1-phenyl-pentanol-5 and/or (iii) one or more butanoyl cyclohexane derivatives of our invention (hereinafter referred to as phenyl alkanol ester-containing composition of matter) are used as perfume adjuvants, the nature of the co-ingredients included with said phenyl alkanol ester-containing compositions of matter in formulating the product composition will also serve to alter the organoleptic characteristics of any ultimate perfumed article treated therewith.

As used herein, the terms "alter" and "modify" in their various forms mean supplying or imparting a perfume aroma character or note to otherwise bland substances or augmenting the existing aroma characteristic where a natural aroma is deficient in some regard or supplementing the existing aroma impression to modify its quality, character or aroma.

As used herein, the term "enhance" is intended to mean the intensification (without effecting a change in the kind or quality of aroma) of one or more aroma nuances and their organoleptic impression of a perfume, perfume composition, cologne or one or more perfumed articles.

The phenyl alkanol ester-containing composition of matter of our invention and one or more auxiliary perfume ingredients, including, for example, alcohols (other than the 3-methyl-1-phenyl-pentanol-5 or compound having the sructure:

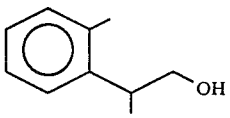

of our invention), aldehydes, ketones other than the butanoyl cyclohexane derivatives of our invention, nitriles, esters (other than the compounds defined according to the structure:

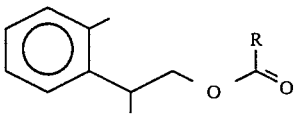

of our invention), lactones, natural essential oils and synthetic essential oils may be admixed so that the combined odors of the individual components produce a pleasant and desired fragrance particularly and preferably in the green, rose, floral, peony-like, hyacinth, anise-like and lilac fragrance areas. It is to be understood that such additional adjuvants are to be organoleptically compatible with the compounds defined according to the structure:

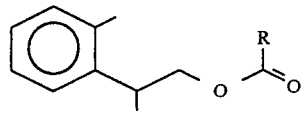

wherein R is methyl or ethyl; said compound defined according to the structure:

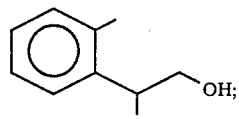

said 3-methyl-1-phenyl-pentanol-5; and one or more of said butanoyl cyclohexane derivatives of our invention, and further that such adjuvants are to be non-reactive under use conditions at room temperature and storage conditions with the said compounds having the structure:

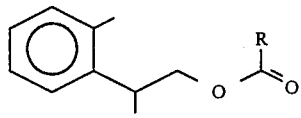

wherein R represents methyl or ethyl, and with the said compound having the structure:

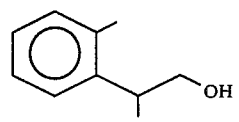

and with the said 3-methyl-1-phenyl-pentanol-5 and with the said butanoyl cyclohexane derivatives of our invention.

Such perfume compositions usually contain (a) the main note or the bouquet or foundation stone of the compositions, (b) modifiers which round off and accompany the main note, (c) fixatives which include odorous substances which lend a particular note to the perfume throughout all stages of evaporation and substances which retard evaporation and (d) topnotes which are usually low-boiling, fresh-smelling materials.

In perfume compositions, it is the individual components which will contribute their particular characteristics; and these individual components will also alter, modify or enhance the overall effect of the perfume composition. Thus the phenyl alkanol ester-containing composition of matter of our invention can be used to alter, augment or enhance the aroma characteristics of a perfume composition, for example, by utilizing or modifying the olfactory reaction contributed by one or more other ingredients in the composition.

The amount of phenyl alkanol ester-containing composition of matter of our invention which will be effective in perfume compositions depends upon many factors including the other ingredients, their amounts and the effects which are desired. It has been found that perfume compositions containing as little as 0.01% of the phenyl alkanol ester-containing composition of matter of our invention and even less (e.g. 0.005%) can be used to impart a green, rose, peony-like, floral, hyacinth, anise-like and lilac aroma to cosmetics and other products including fabric softener articles used in clothes driers. The amounts employed can range up to 10% of the fragrance components and will depend on considerations of cost, nature of the end product, the effect desired on the finished product and the particular fragrance sought.

The phenyl alkanol ester-containing compositions of matter of our invention are useful taken alone or in perfume compositions as an olfactory component in anionic, cationic, nonionic and zwitterionic detergents and soaps, space odorants and deodorants, perfumes, colognes, toilet water, bath preparations such as bath oils and bath solids; hair preparations such as lacquers, brilliantines, pomades and shampoos; cosmetic preparations such as creams, deodorants, hand lotions and sun screens; powders such as talcs, dusting powders, face powders and the like. When used as an olfactory component in a perfumed article, as little as 0.25% of the phenyl alkanol ester-containing compositions of matter of our invention and up to 3% of the phenyl alkanol ester-containing compositions of matter of our invention based on the ultimate end product may be used.

In addition, the perfume composition or fragrance composition of our invention can contain a vehicle or carrier for the phenyl alkanol ester-containing composition of matter of our invention. The vehicle can be a liquid such as a non-toxic alcohol (e.g. 95% food grade ethanol), a non-toxic glycol (e.g. propylene glycol) or the like. The carrier can also be an absorbent solid such as a gum (e.g. gum arabic, xanthan gum or guar gum) or components for encapsulating the composition as by coacervation using gelatin or by forming a polymer wall around a liquid perfume center as by using a urea formaldehyde prepolymer to form a urea formaldehyde polymeric capsule.

The following examples are illustrative and the invention is to be considered to be restricted thereto only as indicated in the appended claims. All parts and percentages given herein are by weight unless otherwise specified.

EXAMPLE I

Reaction:

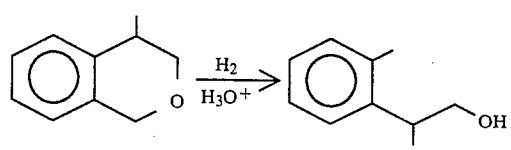

(The reactant having the structure:

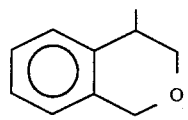

is prepared according to the reactions:

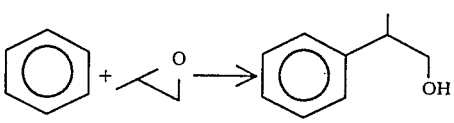

and

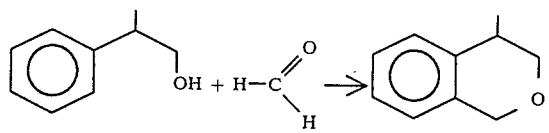

well known in the prior art.)

Into a 500 cc autoclave is placed 300 grams of the compound defined according to the structure:

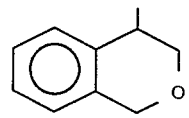

150 grams isopropyl alcohol, 3 grams 5% palladium-on-carbon catalyst, 3 grams phosphoric acid.

Hydrogen is pumped into the autoclave after it is closed while maintaining the reaction temperature at 80°–90° C. and the pressure at 450 psig. The hydrogenation is carried out over a period of 5 hours. At the end of the 5 hour period the autoclave was opened and cooled. The resulting product was filtered. The isopropyl alcohol was stripped from the reaction mass and the resulting reaction product was distilled yielding 262.8 grams of distillate. The distillation was carried out on a 12" Vigreux column yielding the following fractions:

| Fraction Number | Vapor Temp. (°C.) | Liquid Temp. (°C.) | Vacuum mm/Hg |
|---|---|---|---|
| 1 | 119 | 127 | 30 |
| 2 | 115 | 122 | 20 |
| 3 | 116 | 123 | 20 |
| 4 | 116 | 123 | 20 |
| 5 | 116 | 123 | 20 |
| 6 | 117 | 124 | 20 |
| 7 | 117 | 124 | 20 |
| 8 | 117 | 124 | 20 |
| 9 | 118 | 125 | 20 |
| 10 | 118 | 125 | 20 |
| 11 | 118 | 125 | 20 |
| 12 | 117 | 125 | 20 |
| 13 | 118 | 129 | 20 |
| 14 | 118 | 132 | 20 |
| 15 | 118 | 137 | 20 |
| 16 | 110 | 148 | 20 |

Figure 1:
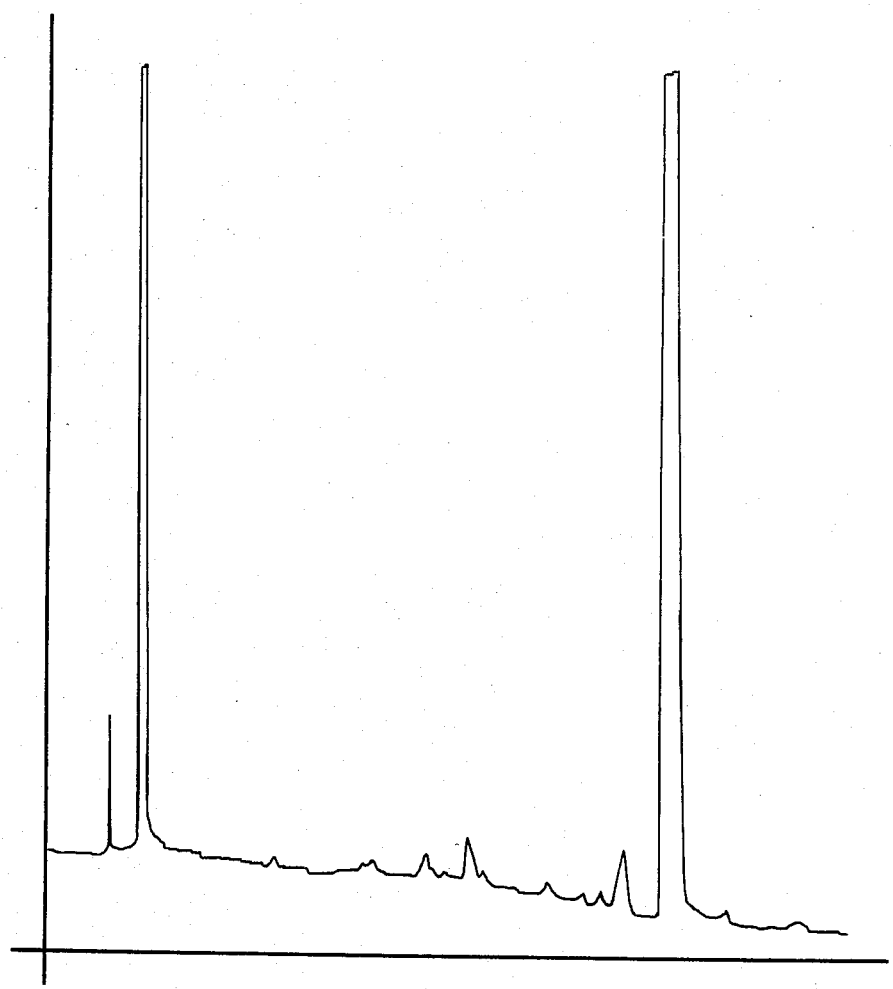
FIG. 1 is the GLC profile for the reaction product of Example I containing the compound defined according to the structure.

FIG. 1 is the GLC profile for the reaction product immediately prior to distillation (conditions: 0.25"×10' 10% Carbowax column programmed at 80°–225° C. at 8° C. per minute).

FIG. 2 is the NMR spectrum for fraction 10 of the foregoing distillation (conditions: CFCl₃ solvent; 100 MHz field strength).

FIG. 3 is the infra-red spectrum for fraction 10 of the foregoing distillation product.

Bulked fractions 6–10 have an extremely strong rose, floral, hyacinth and lilac aroma profile.

EXAMPLE II

PREPARATION OF METHYL HYDRATROPIC ACETATE

Reaction:

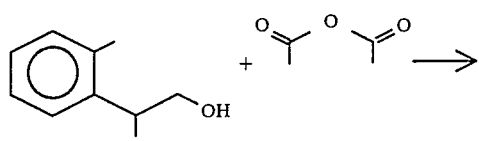

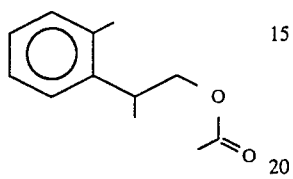

Into a 1 liter reaction vessel equipped with stirrer, thermometer, reflux condenser and heating mantle is placed 252 grams of the compound defined according to the structure:

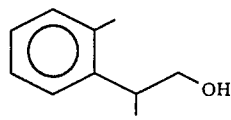

(bulked fractions 6-10 produced according to Example I) and 202 grams of acetic anhydride. The reaction mass is then refluxed at 140° C. for a period of 0.75 hours. At the end of the 0.75 hour period, the reaction mass is cooled to 80° C. and admixed with 500 ml water.

The resulting reaction product now exists in two phases; an organic phase and an aqueous phase. The organic phase is washed with two volumes of water and is then distilled on a 12" Goodloe column yielding the following fractions:

| Fraction Number | Vapor Temp. (°C.) | Liquid Temp. (°C.) | Vacuum mm/Hg. | Weight of Fraction (grams) |
|---|---|---|---|---|
| 1 | 37/76 | 112/108 | 1.4/1.0 | 20.0 |
| 2 | 82 | 108 | 1.0 | 21.6 |
| 3 | 82 | 108 | 1.0 | 21.2 |
| 4 | 82 | 108 | 1.0 | 228 |
| 5 | 82 | 108 | 1.0 | 268 |
| 6 | 82 | 108 | 1.0 | 325 |
| 7 | 82 | 110 | 1.0 | 261 |
| 8 | 82 | 110 | 1.0 | 21.0 |
| 9 | 82 | 112 | 1.0 | 24.3 |
| 10 | 82 | 115 | 1.0 | 26.1 |
| 11 | 82 | 118 | 1.0 | 22.5 |
| 12 | 83 | 120 | 1.0 | 22.4 |
| 13 | 87 | 180 | 1.0 | 15.2 |
| 14 | 80 | 210 | 1.0 | 1.4 |

The resulting has an interesting strong, long lasting, green, floral, peony-like, rosy, hyacinth-like and lilac aroma profile with anise-like undertones.

FIG. 4 is the GLC profile for the crude reaction product prior to distillation.

FIG. 5 is the GLC profile for fraction 9 of the foregoing distillation.

FIG. 6 is the NMR spectrum for fraction 9 of the foregoing distillation (conditions: $CFCl_3$ solvent; 100 MHz field strength).

FIG. 7 is the infra-red spectrum for fraction 9 of the foregoing distillation product containing the compound having the structure:

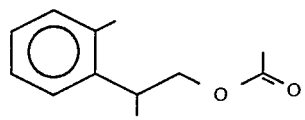

When replacing the acetic anhydride in the foregoing example with propionic anhydride, a product having the structure:

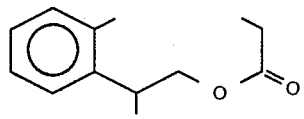

is produced having a green, rose, hyacinth-like, peony-like and lilac aroma profile.

EXAMPLE III

ROSE FORMULATION

The following mixture is prepared:

| Ingredient | Parts by Weight |
|---|---|
| Rhodinol | 270.0 |
| Nerol | 90.0 |
| Linalool | 30.0 |
| Terpineol | 30.0 |
| Phenylethyl alcohol | 12.0 |
| Terpinenol | 5.0 |
| Linalyl acetate | 1.5 |
| Citronellyl acetate | 15.0 |
| Geranyl acetate | 10.0 |
| Eugenol | 33.0 |
| Citral | 15.0 |
| Phenylethyl acetate | 20.0 |
| Rose oxide | 8.0 |
| Guaiacol | 30.0 |
| l-citronellal | 90.0 |
| Neryl acetate | 3.0 |
| Clove bud oil | 1.0 |
| Cadinene | 2.0 |
| Guaiene | 1.0 |
| Gum turpentine | 12.0 |
| Alpha-pinene | 1.0 |
| Myrcene | 5.0 |
| Limonene | 2.0 |
| p-cymene | 1.0 |

To the foregoing formulation 30 parts by weight of the compound defined according to the structure:

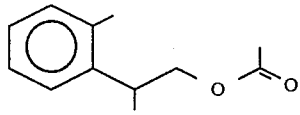

is added (bulked fractions 6-10 of the distillation product of the reaction product of Example II). The resulting mixture has a much brighter, green, rose, hyacinth, peony-like and lilac topnote and anise-like undertone and is richer on dryout as compared with the same mixture without the compound defined according to the structure:

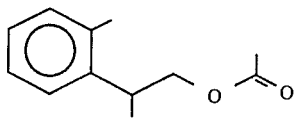

The formulation can thus be described as "intense green, rose, floral aroma with hyacinth, peony and lilac topnotes and anise-like undertones".

EXAMPLE IV

ROSE FORMULATION

The following mixture is prepared:

| Ingredients | Parts by Weight |
|---|---|
| Rhodinol | 270.0 |
| Nerol | 90.0 |
| Linalool | 30.0 |
| Terpineol | 30.0 |
| Phenylethyl alcohol | 12.0 |
| Terpinenol | 5.0 |
| Linalyl acetate | 1.5 |
| Citronellyl acetate | 15.0 |
| Geranyl acetate | 10.0 |
| Eugenol | 33.0 |
| Citral | 15.0 |
| Phenylethyl acetate | 20.0 |
| Rose oxide | 8.0 |
| Guaiacol | 30.0 |
| l-citronellal | 90.0 |
| Neryl acetate | 3.0 |
| Clove bud oil | 1.0 |
| Cadinene | 2.0 |
| Guaiene | 1.0 |
| Gum turpentine | 12.0 |
| Alpha-pinene | 1.0 |
| Myrcene | 5.0 |
| Limonene | 2.0 |
| p-cymene | 1.0 |

To the foregoing formulation 30 parts by weight of a mixture containing a 0.1:1:1:1 (mole ratio) mixture of:
(a) compound having the structure:

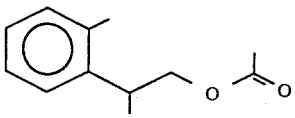

(b) compound having the structure:

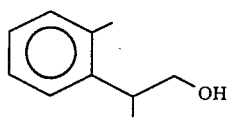

(c) 3-methyl-1-phenyl-pentanol-5
(d) beta-damascenone.

The resulting mixture has a still brighter green, rose topnote and is fruitier and richer on dryout as compared with the same mixture as Example III. Although the resultant mixture has an intense green, rose, hyacinth and lilac topnote profile, it is much more natural-like than the product of Example III which, in turn, is much more natural-like and richer than the product without the compound having the structure:

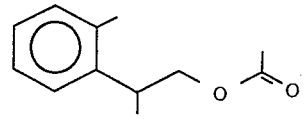

In summary, the product of this example can be described as "fresh rose having a fruity and rich dryout and a very intense hyacinth, peony and lilac topnote and anise-like undertone".

EXAMPLE V

ROSE FORMULATION

The following mixture is prepared:

| Ingredients | Parts by Weight |
|---|---|
| Rhodinol | 270.0 |
| Nerol | 90.0 |
| Linalool | 30.0 |
| Terpineol | 30.0 |
| Phenylethyl alcohol | 12.0 |
| Terpinenol | 5.0 |
| Linalyl acetate | 1.5 |
| Citronellyl acetate | 15.0 |
| Geranyl acetate | 10.0 |
| Eugenol | 33.0 |
| Citral | 15.0 |
| Phenylethyl acetate | 20.0 |
| Rose oxide | 8.0 |
| Guaiacol | 30.0 |
| l-citronellal | 90.0 |
| Neryl acetate | 3.0 |
| Clove bud oil | 1.0 |
| Cadinene | 2.0 |
| Guaiene | 1.0 |
| Gum turpentine | 12.0 |
| Alpha-pinene | 1.0 |
| Myrcene | 5.0 |
| Limonene | 2.0 |
| p-cymene | 1.0 |

To the foregoing formulation 30 parts by weight of a mixture containing a 0.1:1:1:1 (mole ratio) mixture of:
(a) compound having the structure:

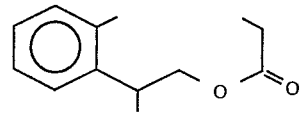

(b) compound having the structure:

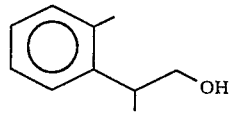

(c) 3-methyl-1-phenyl-pentanol-5
(d) trans,trans-delta damascone.

The resulting mixture has a still brighter rose topnote and is fruitier and richer on dryout as compared with the same mixture as Example III. Although the resultant mixture has an intense green, rose, hyacinth, peony-like and lilac topnote profile, it is much more natural-like than the product of Example III which, in turn, is much more natural and richer than the product without the compound having the structure:

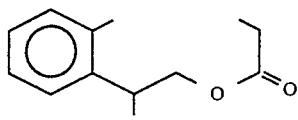

In summary, the product of this example can be described as "fresh, newly blossomed rose having a fruity and rich dryout and a very intense peony-like, hyacinth and lilac topnote".

EXAMPLE VI

PREPARATION OF A SOAP COMPOSITION

One hundred grams of soap chips are prepared according to Example V of U.S. Pat. No. 4,058,490 issued on Nov. 15, 1977, the specification for which is incorporated by reference herein as follows:

"The sodium salt of an equal mixture of $C_{10}/C_{14}$ alkane sulfonates (95% active), 40 lbs. is dissolved in a mixture of 80 lbs. of anhydrous isopropanol and 125 lbs. of deionized water at 150° F. In this mixture is dissolved 10 lbs. of partially hydrogenated coconut oil fatty acids and 15 lbs of sodium mono-$C_{14}$-alkyl maleate, and the pH of this solution is adjusted to 6.0 by the addition of a small amount of a 50% aqueous solution of NaOH. The isopropanol is distilled off and the remaining aqueous solution is drum dried. The resulting solid actives are then blended in a chip mixer with 10 lbs. water, 0.2 lbs. titanium hydroxide"

are mixed with one gram of one of the perfumery materials as set forth in Table I below until a substantially homogeneous composition is obtained. The perfumed soap composition manifests an excellent aroma as set forth in Table I below:

TABLE I

| Perfumery Composition | Aroma Profile |
|---|---|
| Product having the structure: (as shown) produced according to Example II, bulked fractions 6-10. | An intense green, rose, hyacinth, peony-like, floral and lilac aroma profile with anise-like undertones. |
| Perfume composition of Example III. | An intense green, rose, floral aroma with hyacinth, peony and lilac topnotes and anise-like undertones. |
| Perfume composition of Example IV. | Fresh rose having a fruity and rich dryout and a very intense hyacinth, peony and lilac topnote and anise-like undertone. |
| Perfume composition of Example V. | Fresh, newly blossomed rose having a fruity and rich dryout and a very intense peony-like, hyacinth and lilac topnote. |

EXAMPLE VII

PREPARATION OF A DETERGENT COMPOSITION

A total of 100 grams of detergent powder prepared according to U.S. Pat. No. 4,058,472, the specification for which is incorporated by reference herein and containing 5% by weight of the sodium salts of a mixture of sulfonated $C_{14}-C_{18}$ alkyl catechol as a surface active component, the mixture being 60 parts by weight of mono-$C_{14}-C_{18}$ alkyl catechol, 35% sodium tetrapyrrole phosphate, 30% of sodium carboxymethylcellulose and 7% of starch is mixed with 0.15 grams of one of the perfumery materials set forth in Table I of Example VI until a substantially homogeneous composition is obtained. This composition has an excellent aroma as set forth in Table I of Example VI.

EXAMPLE VIII

PERFUMED LIQUID DETERGENT

Concentrated liquid detergents each with an aroma as set forth in Table I of Example VI containing 0.10%, 0.15% and 0.20% of the perfumery materials of Table I of Example VI are prepared. They are prepared by adding and homogeneously mixing the appropriate quantity of perfumery material as set forth in Table I of Example VI in the liquid detergent. The detergents all possess aromas as set forth in Table I of Example VI.

EXAMPLE IX

PREPARATION OF A COLOGNE AND HANDKERCHIEF PERFUME

The compositions as set forth in Table I of Example VI are incorporated into colognes at concentrations of 1.5%, 2.0%, 2.5%, 3.0%, 4.0% and 5.0% in 75%, 80%, 85% and 90% aqueous ethanol or diethyl phthallate and into handkerchief perfumes at concentrations of 15%, 20%, 25% and 30% (in 90% and 95% aqueous ethanol). The use of the perfumery materials of Table I of Example VI afford distinct and definitive strong aromas as set forth in Table I of Example VI in the handkerchief perfume and in the cologne.

EXAMPLE X

PREPARATION OF A COSMETIC POWDER COMPOSITION

A cosmetic powder is prepared by mixing in a ball mill 100 grams of talcum powder with 0.15 grams of the compositions of matter as set forth in Table I of Example VI supra. Each of the compositions has an excellent aroma as set forth in Table I of Example VI.

EXAMPLE XI

Utilizing the procedure of Example I at column 15 of U.S. Pat. No. 3,632,396, the specification for which is incorporated herein by reference, a non-woven cloth substrate useful as a drier added fabric softening article of manufacture is prepared wherein the substrate, the substrate coating and the outer coating and the perfuming material are as follows:
1. a water "dissolvable" paper ("Dissolvo Paper");
2. Adogen 448 (melting point about 140° F.) as the substrate coating; and
3. an outer coating having the following formulation (melting point about 150° F.):
    57% $C_{20-22}$ HAPS
    22% isopropyl alcohol
    20% antistatic agent
    1% of one of the perfumery materials set forth in Table I of Example VI giving rise to aroma nuances in the head space above a clothing batch dried using this drier-added fabric softener as set forth in Table I of Example VI, supra.

Fabric softener compositions prepared as set forth above giving rise to the aroma characteristics set forth in Table I of Example VI consist of a substrate having a weight of about 3 grams per 100 square inches, a substrate coating of about 1.85 grams per 100 square inches of substrate and an outer coating of about 1.4 grams per 100 square inches of substrate thereby providing a total aromatized substrate and outer coating weight ratio of about 1:1 by weight of the substrate. As stated supra, the aromas set forth in Table I of Example VI are imparted in a pleasant manner to the head space in the drier on operation thereof using the said drier added fabric softening non-woven fabric.

What is claimed is:

1. The composition comprising the compound defined according to the structure:

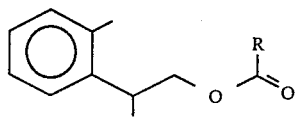

wherein R is methyl or ethyl and, intimately admixed therewith, a compound selected from the group consisting of:

(a) a compound having the structure:

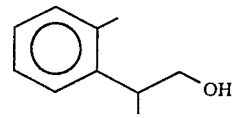

(b) 3-methyl-1-phenyl-pentanol-5; and (c) at least one butanoyl cyclohexane derivative defined according to the structure:

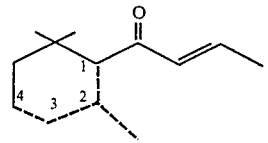

wherein one or two of the dashed lines represent carbon-carbon double bonds and the other of the dashed lines represent carbon-carbon single bonds with the proviso that when the dashed lines represent two carbon-carbon double bonds, said carbon-carbon double bonds are conjugated.

2. A process for augmenting or enhancing the aroma of a consumable material selected from the group consisting of perfume compositions, colognes and perfumed polymers comprising the step of adding to said consumable material an aroma augmenting or enhancing quantity of the composition defined according to claim 1.